US00PP10669P

United States Patent [19]

Lane

[11] Patent Number: Plant 10,669

[45] Date of Patent: Nov. 3, 1998

[54] APPLE TREE 'CHINOOK'

[75] Inventor: W. David Lane, Summerland, Canada

[73] Assignee: okanagan Plant Improvement Co.Ltd., Summerland, Canada

[21] Appl. No.: 879,119

[22] Filed: Jun. 19, 1997

[51] Int. Cl.[6] ..... A01H 5/00

[52] U.S. Cl. ..... Plt./34.1

[58] Field of Search ..... Plt./34.1

*Primary Examiner*—James R. Feyrer

*Attorney, Agent, or Firm*—Okanagan Plant Improvement Co. Ltd.

[57] ABSTRACT

A new and distinct variety of apple tree, originating from a controlled cross of 'Splendour' and 'Gala', substantially illustrated and described, which is most similar to 'Fuji'. The variety is distinguished by the small to medium sized fruit with the skin having 80% to 90% pink/red blush over a yellow ground, and large white lenticels The flesh is yellow, crisp, firm, and juicy. The fruit is short globose conical in shape, with little or no ribbing, weak crowning of the distal end and a long stem. The variety was named 'Chinook' in 1997.

2 Drawing Sheets

BACKGROUND OF THE INVENTION

Field of Invention

This invention relates to apple trees and particularly to a seedling apple tree from a controlled cross made at the Pacific Agri-Food and Agriculture Research Centre Summerland apple breeding program located at Summerland, British Columbia, Canada.

Following initial testing of the tree of this disclosure, and with the recognition that it is a productive bearer of dessert quality apples, this apple (*Malus ×domestica*) tree was named 'Chinook'.

The Agriculture and Agri-Food Canada research facility at Summerland was established in 1914. Originally called the Dominion Experimental Farm at Summerland, the name was changed to the Summerland Research Station in 1959, the Summerland Research Centre in 1994 and to the Pacific Agri-Food Research Centre Summerland in 1996. The tree fruit breeding program was established in 1924 to provide new varieties for the tree fruit industry of British Columbia, Canada, and the world. The breeding program at Summerland has produced several tree fruit varieties including 'Spartan', 'Summerred' and 'Sunrise' apples and 'Van', 'Lapins' and 'Sweetheart' cherries. The tree fruit breeders typically produce several thousand hybrid seedlings each year. Evaluations begin upon fruiting. The uppermost non-terminal buds of the non-fruiting seedlings are budded onto rootstocks, to induce earlier fruiting, in "seedling" fields. Upon fruiting the varieties are evaluated for appearance, taste, texture, harvest indices of the fruit, and disease susceptibility and growth habit of the tree in the field. Promising seedlings are repropagated in replications of 4 to 6 trees, by budding or grafting onto rootstocks and planted out as first selections in variety evaluation plots. The reproductions are evaluated for varietal stability, disease susceptibility, and fruit and tree quality. The most promising selections are re-propagated and planted out in randomized second selection evaluation plots complete with standards. Upon fruiting, second selections are evaluated for varietal stability, and for taste, texture and appearance of the fruit, by conducting "in-house" sensory evaluation panels. At this time new varieties are compared to reference varieties to establish uniqueness.

The present invention relates to a new and distinct variety of apple tree which was named 'Chinook' in January 1997 by Dr. H.A Quamme. 'Chinook' is the result of a controlled cross of the seed parent 'Splendour' (a chance seedling found in Napier New Zealand in 1964) and the pollen parent 'Gala' (a cross of 'Kidd's Orange Pippin'×'Golden Delicious' from J.H. Kidd at Wairarapa, New Zealand. The original cross was made in 1980 by breeder Dr. D.A. Lane and the seedling was planted in 1981. The seedling was propagated by budding onto rootstocks in "seedling" blocks in 1983. It was given the breeder's reference number '8S-27-51' at this time. '8S-27-51' was selected and further propagated by budding in 1990. Six propagations were planted in second selection variety test plots in 1991. The fruit and plant characteristics were true to the original plant in all respects. The variety was selected on the criteria of tree growth habit, appearance, taste and texture. '8S-27-51' was further propagated in 1990 and planted out in randomized evaluation plots in 1992 with 'Fuji' as a reference variety. Controlled grower trials under test agreement have been established in British Columbia. '8S-27-51' was named 'Chinook' in 1997 by breeder Dr. H.A. Quamme.

Distinguishing Characteristics

The variety 'Chinook' is a mid-to late-season apple, maturing about the first to second week of October at Summerland. The skin color is an 80 to 90% pink/red blush overcolor on a yellow ground. The skin has a bright luster, and large white lenticels. Some stem bowl russeting is present, but it does not usually extend past the shoulders of the fruit. The fruit of 'Chinook' is short globose-conical in shape, and small to medium in size, averaging 6.8 cm in diameter and 170 to 180 grams in weight. The fruit has little or no ribbing and weak crowning of the distal end. The fruit stem is long, averaging 31 mm. The flesh of 'Chinook' is crisp, firm (a pressure of 18–19 lbs at maturity), juicy and yellow. The soluble solids content of 'Chinook' at maturity is about 11% to 13%. The tree is of moderate to low vigor, spreading, precocious and productive. Trials indicate that 'Chinook' will store for 3 months in 0° C. air and 5 months in 0° C. controlled atmosphere (C.A.) storage.

Parent Plants

'Chinook' is the result of a controlled cross of the seed parent 'Splendour' and the pollen parent 'Gala'.

'Splendour' is a chance seedling of unknown parentage, found by C.L. Roberts in Napier, New Zealand in 1948 and named in 1967.

'Chinook' differs from 'Splendour' in that the fruit of 'Splendour' is large, ovoid-conical in shape and slightly ribbed. The skin of 'Splendour' is bright red in color, glossy, and has few lenticels.

'Gala' is the result of a cross of 'Kidd's Orange Pippen'× 'Golden Delicious' from J.H. Kidd at Wairarapa New Zealand and was selected in 1937. 'Kidd's Orange' is a cross of 'Delicious'×'Cox's Orange Pippin', 'Golden Delicious' was developed from a chance seedling discovered in Clay Creek, W. Va. by Andrew H. Mullins.

'Chinook' differs from 'Gala' in that the fruit of 'Gala' matures in early September at Summerland and has a skin groundcolor of pale yellow with an overcolor of red stripes and flecks. The tree of 'Gala' is vigorous and upright.

SUMMARY OF THE INVENTION

The new and distinct variety of Malus fruiting apple tree, 'Chinook', resulted from a cross made in 1980 at the Pacific Agri-Food Research Centre in Summerland, British Columbia, Canada by breeder Dr. D.A. Lane. The variety has been established and is being maintained at the research facility. Evaluations began upon fruiting.

The variety is stable with no variations occurring, and demonstrates significant differences from its parents in that it has pinkish red skin, with prominent white lenticels and is short globose conical in shape. The fruit is very sweet, firm and juicy. The tree is very precocious and productive. The variety matures in mid-to-late season, with harvest dates around October 1st to 7th in Summerland. 'Chinook' was asexually propagated (by budding) in 1983 and established in a "seedling" evaluation plot 'Chinook' has been evaluated from first fruiting in 1986 until 1997 at the Pacific Agri-Food Research Centre, Summerland.

The tree habit is spreading, spurry and moderately vigorous. The test plantings also contained the reference variety 'Fuji' for comparision to 'Chinook',

BRIEF DESCRIPTION OF THE VIEWS OF THE DRAWING

The accompanying photographic drawing comprises two sheets of photographic drawing wherein:

The first sheet, comprises showings of the mature fruit of 'Chinook' in large scale, to depict the blossom end (top left), the stem end (top right), and the side view in two orientations (middle), respectively. At the bottom of the first sheet, on the left, a typical specimen of the fruit is displayed in cross section after being cut on the plane of the fruit axis; and, on the right, a specimen sliced centrally across the core is shown. Depicted are the nearly solid red blush pattern of overcolor and the general absence of ground color and the shape mature fruit. The bottom two photographs show the fruit stem and the internal fruit characteristics of the eye basin, stem cavity, flesh color, core characteristics, carpels and the seed and locules of fruit of 'Chinook'.

On the second sheet, at the top left, a typical branch bearing fruit, at about the stage of maturity for harvest, is shown. This photograph illustrates mature foliage, bark and lenticel character and coloration of bearing wood as well as fruit. On the top right, a similar specimen is depicted showing the spur habit, fruit exposure and folier density of a typical stem. At the bottom, a specimen of the tree is depicted at harvest stage; the compact habit, spur bearing and productivity of the specimen is readily depicted.

TRIALS AND EVALUATIONS

A seedling resulting from a controlled cross made in 1960 was asexually reproduced in 1983 by budding and given the breeders reference number '8S-27-51'. '8S-27-51' was reproduced and planted in cultivated variety blocks, complete with standards at the Pacific Agri-Food Research Centre (PARC) Summerland orchards in 1990. The reproductions have shown 'Chinook' to the stable with no variations occurring. The variety has been observed and evaluated since first fruiting in 1992.

Test plots established at PARC Summerland that included 4 trees of 'Chinook' ('8S-27-51') were established in 1991. The variety was compared to the reference variety 'Fuji' of approximately the same age and the same rootstock planted in the same area. Controlled grower trials, under test agreements, have been established in British Columbia and in selected sites in the United States.

'Chinook' was tested in sensory evaluation panels in 1995 and 1996. Sensory evaluation panels consists of 10 to 12 trained panelists. About 10 apple varieties, including 1 or 2 standards, are rated per session on a hedonic (liking) scale for texture, flavor and appearance. In addition, panelists use a sensory scale to rate the intensity of crispness, hardness, juiciness, sweetness and aromatics. All ratings are on a scale of 0 to 9, with 0 being a low rating and 9 being a high rating.

The standards used in the sensory evaluation panels were 'Fuji', 'Royal Gala' and 'Red Delicious' in 1995–1996. The test plantings also contained the reference varieties 'Fuji' and 'Royal Gala' used for comparison to 'Chinook' in 1995 and 1996 sensory panels 'Chinook' was rated as better than 'Royal Gala', 'Red Delicious' and 'Fuji' in appearance. Flavor was rated better than 'Gala' in 1996 and as good as 'Red Delicious' in 1995. 'Chinook' was sweeter than for 'Red Delicious' and similar to 'Fuji' and 'Gala' in sweetness. 'Chinook' was more sour than for 'Fuji' or 'Gala' in 1996 panels. 'Chinook' was less juicy than 'Fuji' but similar to 'Gala' and 'Red Delicious'. 'Chinook' fruit is harder than 'Gala' and similar to 'Fuji'. The intensity of aroma and crispness did not differ from 'Gala', 'Fuji' or 'Red Delicious'. Texture was rated as better than 'Gala' and as well liked as 'Fuji' and 'Red Delicious'. Initial storage assessments indicate that the fruit of 'Chinook' will store for 3 months in OC storage and 5 months in controlled atmosphere (CA) storage.

Under growing conditions in Summerland B.C 'Chinook' is harvested around October 1st to 7th, about 'Red Delicious' time, at Summerland whereas 'Fuji' is a late season apple maturing late October to early November, after Red Delicious, at Summerland. The fruit of 'Chinook' is small to medium in size, averaging about 68 mm in diameter and 170 to 180 grams in weight. The fruit is short globose-conical in shape, with a skin color 80 to 90% bright pinkish red blush over a yellow ground color. The fruit of 'Fuji' is large in size, averaging 76 mm in diameter and 200 to 260 grams in weight. The fruit is globose conical in shape with a skin color of 70 to 80% brown to pink/red streaks over a yellow/green ground color. The flesh of 'Chinook' is sweet-tart and develops its best flavor in storage. 'Chinook' can develop some stem bowl russeting that does not usually extend past the shoulders The flesh of 'Fuji' is very sweet, firm and moderately juicy. The skin of 'Fuji' can develop russeting over the entire surface of the fruit. The tree habit of 'Chinook' is non-vigorous while 'Fuji' is more vigorous, both varieties are speading and bear fruit on spurs. Storage and maturity trials conducted by Okanagan Federated Shippers (Sam Lau) indicate 'Chinook' will store up 3 months in 0° C. air and 5 months 0° C. Controlled Atmosphere. Lau found 'Fuji' will store up to 4 months at 0° C. air and up to 8 months in 0° C. Controlled Atmosphere.

Pomological Characteristics

'Chinook'

Fruit end use: Dessert.

Growth characteristics

*Tree.*—Trees observed were cultivars of the same age on M9 rootstock in close proximity.
*Vigor.*—Non vigorous.
*Habit.*—Spreading.
*Branch frequency.*—Medium.
*Branch strength.*—Intermediate.
*Angle of bearing branches.*—50–90 degrees.
*Predominance of bearing.*—Spurs.

Shoot Characteristics: Measurements are means of 10 one-year old dormant shoots in 1996.

*Pubescence* (*on upper half*).—Weak.
*Shine of bark.*—Medium.
*Mean diameter* (*center of middle internode*).—4.6 mm.
*Mean internode length.*—18 mm.
*Denisty of lenticels* (*middle third shoot*).—Medium.
*Predominant color of bark* (*on sunny side*).—Reddish brown.
*Position of bud on sheet.*—Appressed.
*Shape of bud.*—Pointed.

Flower characterstics: Measurements are means of 10 flowers.

*Type.*—Single.
*Size* (*pressed flat*).—54 mm.
*Color of bud* (*balloon stage*).—59D/65C (Royal Horticultural Society Colour C).
*Color of upperside of petal.*—63B/155D (R.H.S.).
*Bud burst.*—After 'Jonagold' and before 'Fuji'.
*Petal shape.*—Broad elliptic.
*Petal margins.*—Touching to overlapping.

Leaf characteristics: 4th to 6th fully expanded leaf. Measurements are mean of 20 leaves.

*Shape at cross section.*—Concave.
*Leaf apex.*—Acuminate.
*Leaf margins.*—Serrate.
*Pubescence of upper side.*—Weak.
*Color on upper side of leaf.*—146A (R.H.S.).
*Anthocyanin coloration* (*on under side of leaf*).—Margins and veins only.
*Leaf orientation.*—Upwards.
*Leaf length.*—Mean: 101.3 mm. Range: 86 to 120 mm.
*Leaf width.*—Mean: 49.2 mm. Range: 42–58 mm.
*Leaf blade ratio* (*length/width*).—2.1.
*Petiole length.*—Mean: 27.2 mm. Range: 21–29 mm.
*Ratio leaf length/petiole length.*—3.8.
*Glossiness of upper side.*—Medium to strong.
*Pubescence.*—Slightly pubescent on lower side.
*Stipule size.*—Mean: 10.2 mm. Range: 6–15 mm.

Fruit characterstics: Measurements are the mean to 10 mature fruits.

*Size* (*diameter*).—68.7 mm.
*Average fruit weight.*—170–180 g.
*Shape.*—Short globose conical.
*Symmetry* (*side view*).—Slightly asymmetrical.
*Ribbing.*—Very weak.
*Distal end lobing.*—Weak.
*Depth of eye basin.*—15 mm.
*Width of eye basin.*—30.3 mm.
*Sepal spacing.*—Touching.
*Thickness of stalk.*—1.7 mm.
*Stalk cavity width.*—28.4 mm.
*Stalk cavity depth.*—16.4 mm.
*Stalk length.*—33.1 mm.
*Surface.*—Smooth.
*Bloom of skin.*—Slight.
*Waxiness of skin.*—Slight.
*Ground color.*—5C (R.H.S.).
*Amount of overcolor of skin.*—80–90% (R.H.S.).
*Type of over color.*—Blushed.
*Hue of overcolor of skin.*—53A-53B (R.H.S.).
*Position of russet.*—Stem bowl, does not exceed shoulders.
*Amount of russet.*—Low.
*Size of lenticels on fruit.*—Medium to large.
*Prominence of lenticels.*—Prominent.
*Color of lenticels.*—White.
*Distinctness of core line* (*cross section*).—Weak to medium.
*Aperture of locules.*—Open.
*Spacing of sepals at base.*—Touching.
*Fruit set* (*yield efficiency*).—Very god to excellent.
*Maturity date at Summerland, B.C.*—First week of October.
*Seed color at maturity.*—Brown.
*Soluble solid %.*—11–13% at harvest.
*Titratable acidity.*—500–600 mg malic acid per 100 ml juice.
*Juiciness.*—Medium juiciness.
*Flesh firmness without skin* (*penetrometer*).—19–20 lbs.
*Brownng of flesh* (1hr. *after cutting*).—Medium.

Storage of fruit:

*Air.*—3 months.
*Controlled atmosphere.*—5 months.

We claim:

1. A new and distinct variety of apple tree, originating from a controlled cross of 'Splendour' × 'Gala', substantially illustrated and described and distinguished from other varieties in that the fruit matures mid-to late season, is short globose conical in shape, has pinkish red skin with prominent white lenticels, and is very sweet, firm and juicy.

* * * * *

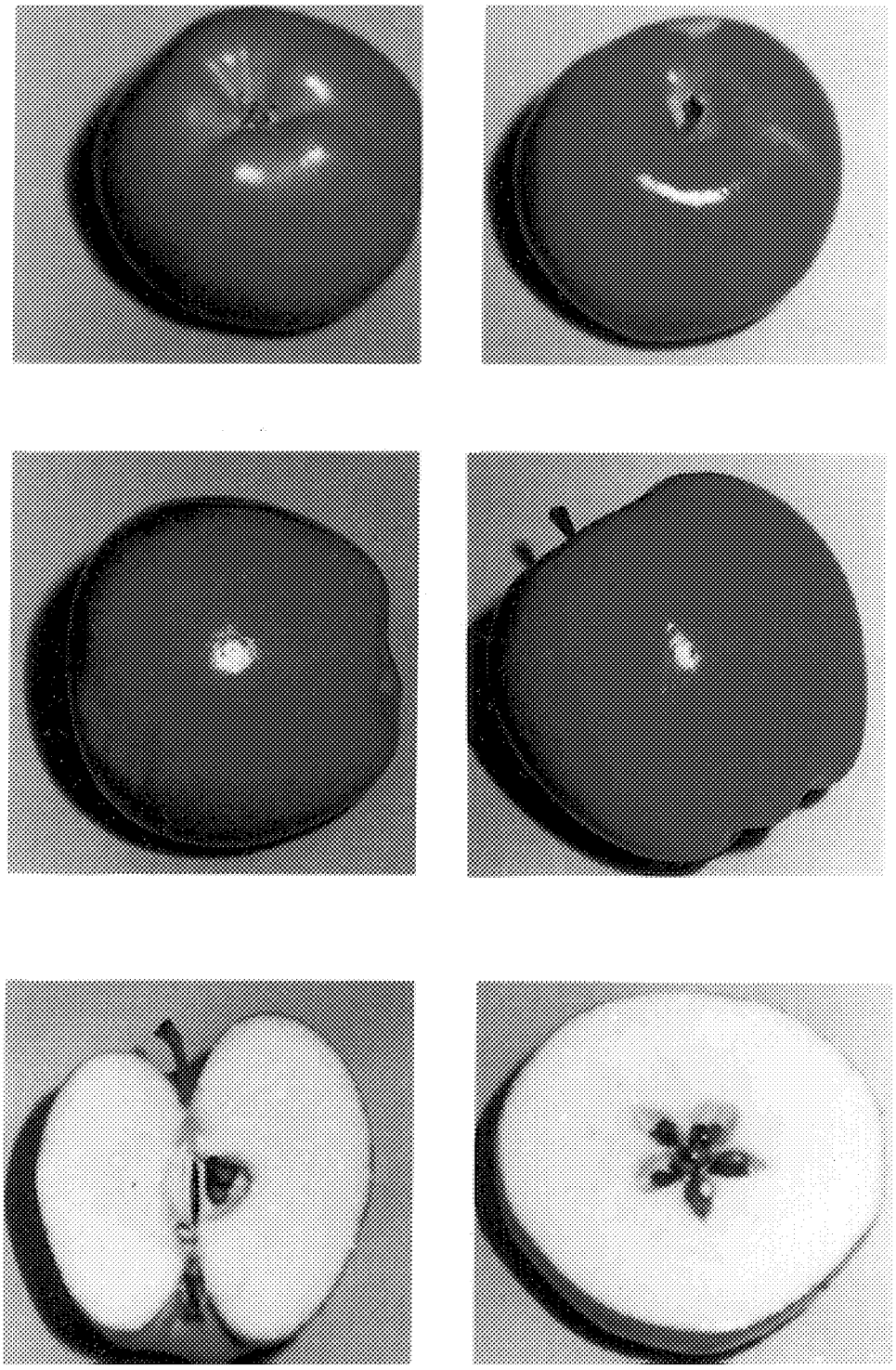

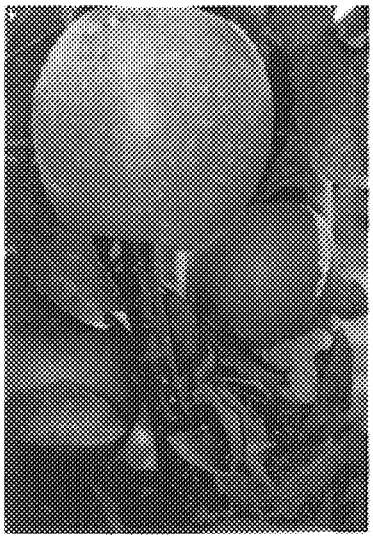
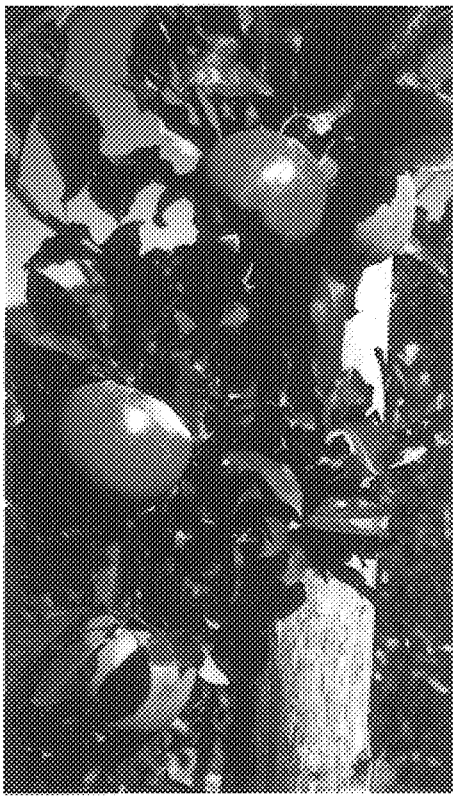
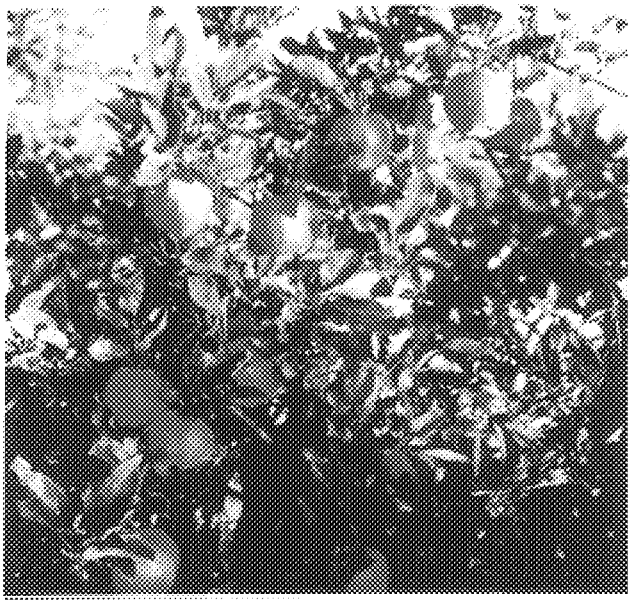

UNITED STATES PATENT AND TRADEMARK OFFICE

CERTIFICATE OF CORRECTION

PATENT NO. : Plant 10,699
DATED : November 24, 1998
INVENTOR(S) : Sam McGredy

It is certified that error appears in the above-identified patent and that said Letters Patent is hereby corrected as shown below:

Column 2, line 29, after "Form." delete the apostrophe-.

Signed and Sealed this

Twenty-ninth Day of February, 2000

*Attest:*

Q. TODD DICKINSON

*Attesting Officer*

*Commissioner of Patents and Trademarks*